United States Patent [19]

Moran

[11] Patent Number: 4,630,276
[45] Date of Patent: Dec. 16, 1986

[54] COMPACT LASER SCANNING SYSTEM

[75] Inventor: Kevin E. Moran, Belmont, N.C.

[73] Assignee: Aeronca Electronics, Inc., Charlotte, N.C.

[21] Appl. No.: 658,603

[22] Filed: Oct. 9, 1984

[51] Int. Cl.$^4$ .................. H01S 3/111; H01S 3/123
[52] U.S. Cl. .................................. 372/15; 372/99; 356/237
[58] Field of Search .................. 372/14, 15, 16, 99, 372/108, 19; 356/237

[56] References Cited

U.S. PATENT DOCUMENTS

| | | |
|---|---|---|
| 2,844,648 | 7/1958 | Rosenthal . |
| 3,531,183 | 9/1970 | Aagard . |
| 3,575,668 | 4/1971 | Smith .................................. 372/19 |
| 3,748,014 | 7/1973 | Belser . |
| 3,752,558 | 8/1973 | Lloyd . |
| 3,782,803 | 1/1974 | Buck . |
| 3,790,246 | 2/1974 | Pickering . |
| 3,790,287 | 2/1974 | Cuthbert et al. .................. 356/237 |
| 3,825,325 | 7/1974 | Hartley et al. . |
| 3,961,838 | 6/1976 | Zanoni . |
| 3,973,833 | 8/1976 | Lawson . |
| 4,054,361 | 10/1977 | Noguchi . |
| 4,108,533 | 8/1978 | Sick et al. . |
| 4,116,527 | 9/1978 | Sick . |
| 4,213,157 | 7/1980 | DeBenedictis et al. . |
| 4,314,763 | 2/1982 | Steigmeier et al. . |
| 4,321,628 | 3/1982 | Crean . |
| 4,355,860 | 10/1982 | Lavallee et al. . |
| 4,376,583 | 3/1983 | Alford et al. ........................ 356/237 |

OTHER PUBLICATIONS

"A Laser Scan Technique for Electronic Material Surface Evaluation", D. R. Oswald and D. F. Munro, published in The Journal of Electronic Materials, vol. 3, No. I, 1974, pp. 225–242.

"Silicon/Analyzer Using A He–Ne Laser", H. J. Ruiz et al, published in The Journal of Electro Chemical Society: Solid State Science and Technology, May 1974, pp. 689–692.

Xerox Disclosure Journal, vol. 5, No. 4, Jul./Aug. 1980, pp. 429–430.

Primary Examiner—William L. Sikes
Assistant Examiner—Robert E. Wise
Attorney, Agent, or Firm—Bell, Seltzer, Park & Gibson

[57] ABSTRACT

The present invention provides a laser scanning system of compact size and relatively long focal length which may be used in laser surface inspection system for silicon wafers and the like. The scanning system employs a folded optical cell having a pair of reflective surfaces so oriented that the scanning laser beam is folded, and reflects from each of the reflective surfaces several times to significantly increase the focal length. The folded optical cell is also effective to produce a collimated, substantially parallel scan pattern such that the beam remains perpendicular to the inspection surface as it is scanned. The folded optical cell can also be set for divergent or convergent scan.

13 Claims, 6 Drawing Figures

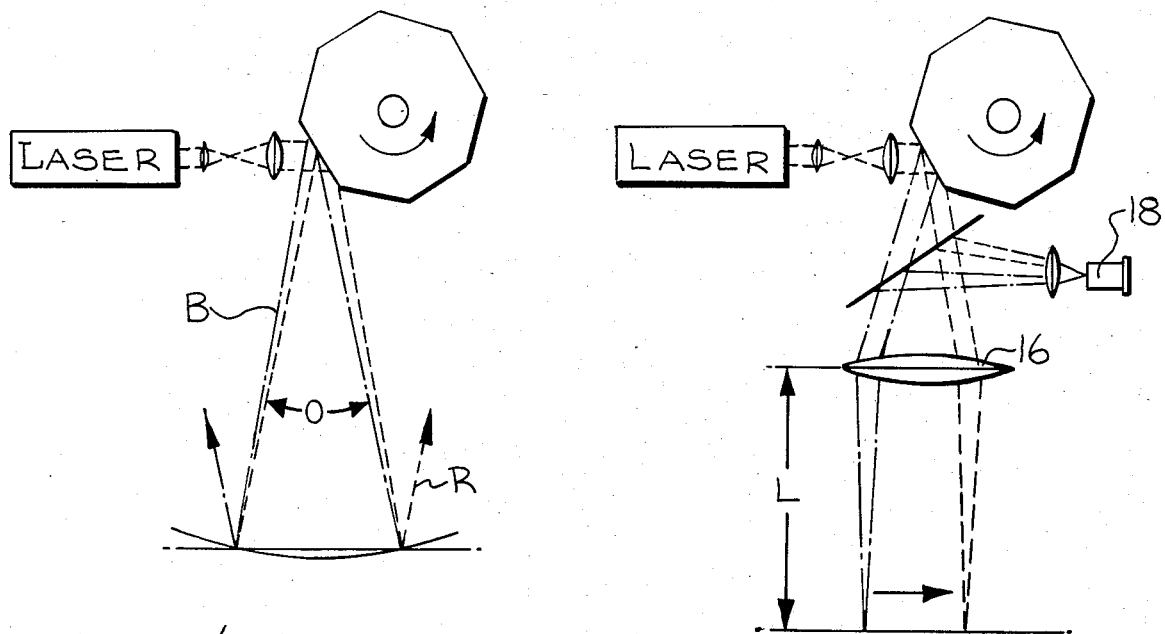
Fig-1 (PRIOR ART)
Fig-2 (PRIOR ART)
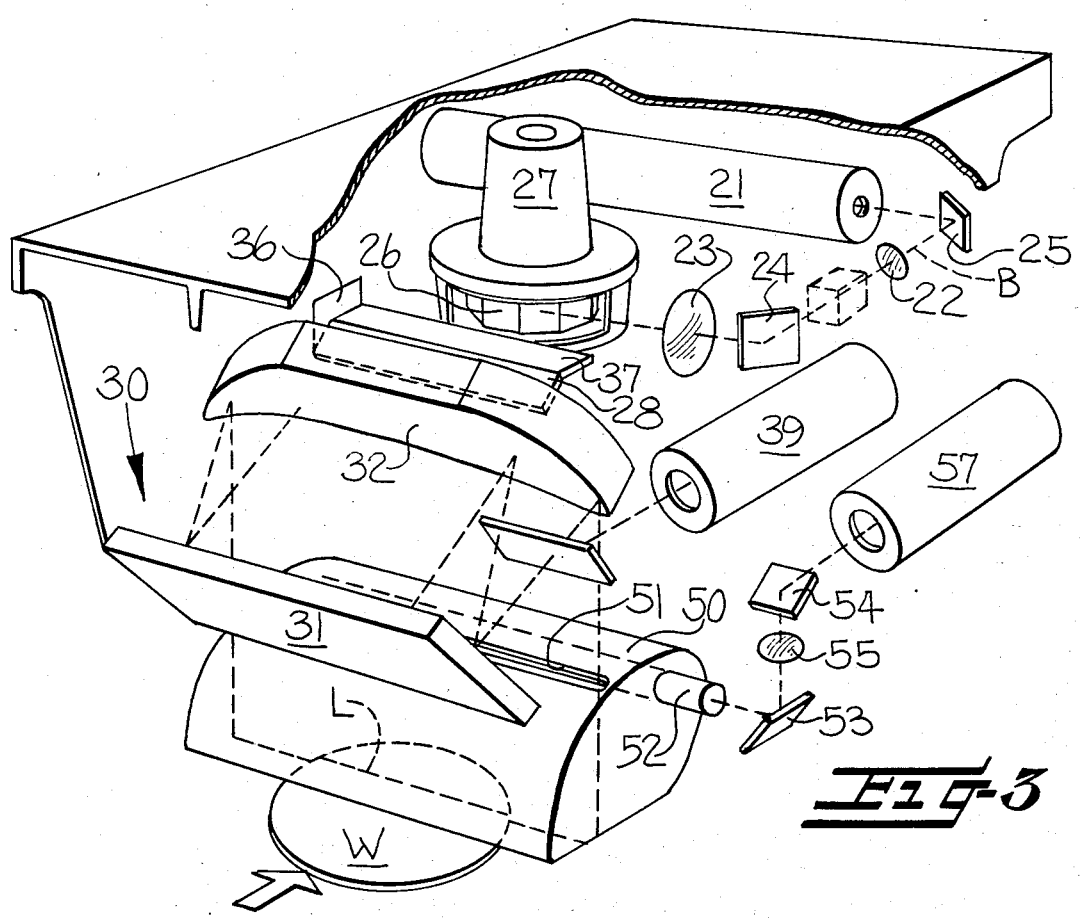
Fig-3

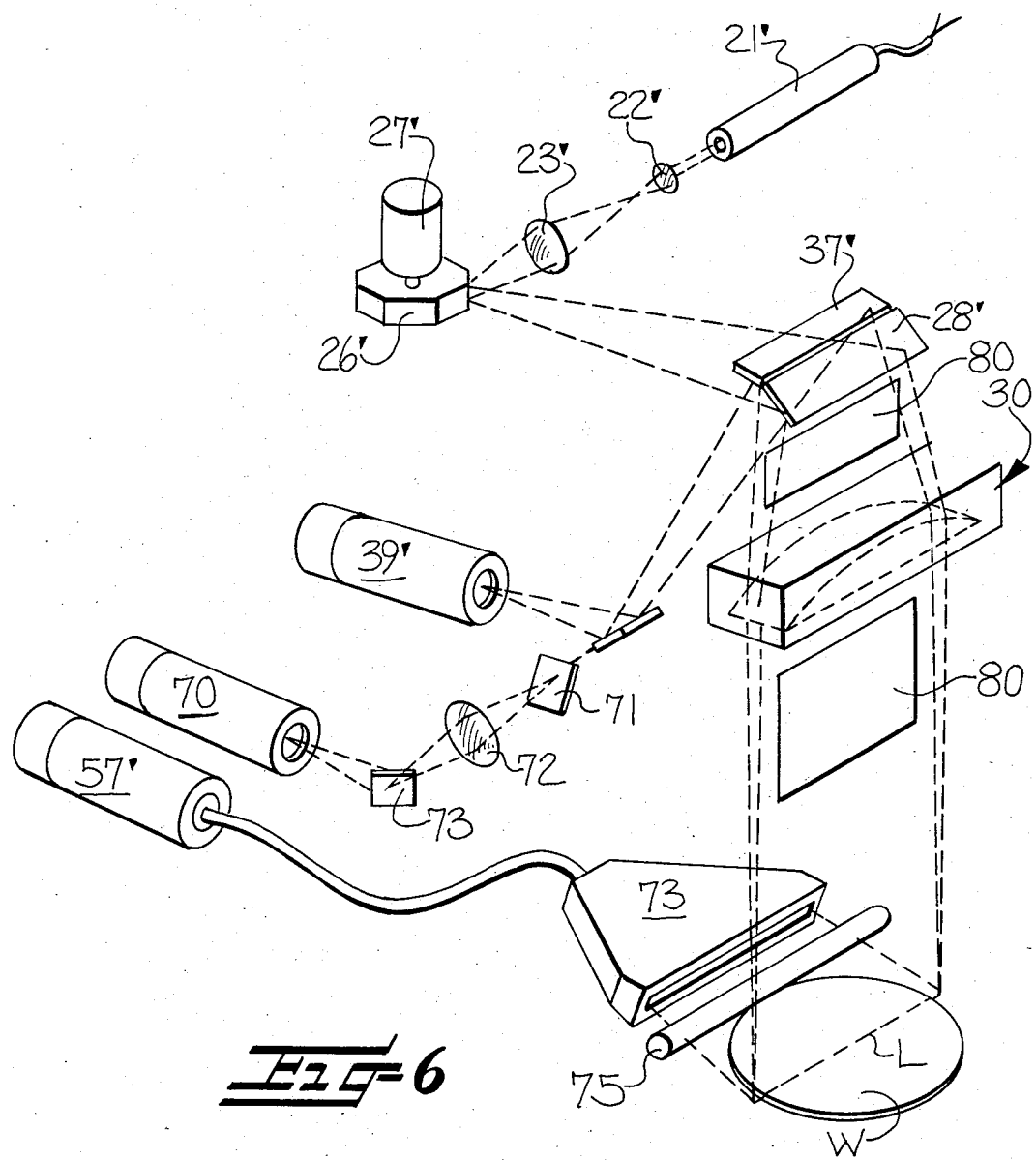

COMPACT LASER SCANNING SYSTEM

FIELD AND BACKGROUND OF THE INVENTION

This invention relates to a laser scanning system and to a laser surface inspection system in which a scanning laser beam is employed for optically detecting microscopic defects in a specularly reflecting surface, such as a silicon wafer.

Silicon wafer discs are used by semiconductor manufacturers as the base substrate in the manufacture of solid state electronic components, such as integrated circuits. The presence of any small defects, such as scratches, pits, or crystal imperfections in the surface, or the presence of surface contaminants such as fingerprints, dust or dirt is highly undesirable and adversely affects the yield of the individual components in production.

Heretofore, silicon wafers have been inspected for flaws or defects by a manual visual inspection technique in which a human inspector visually examines the wafer under an intense light. More recently, automated silicon wafer inspection systems have been developed which are capable of detecting imperfections of a much smaller size than could be detected with the manual visual inspection method. Typically, the automated silicon wafer inspection systems employ a scanning laser beam to inspect the silicon wafers. Laser surface inspection systems of this type have been described for example in an article entitled "A Laser Scan Technique For Electronic Material Surface Evaluation" by D. R. Oswald and D. F. Monroe, published in *The Journal of Electronic Materials,* Volume 3, No. 1, 1974, pages 225-241; in an article entitled "Silicon/Analyzer Using A He-Ne Laser" by H. J. Ruiz et al, published in *The Journal of Electro Chemical Society: Solid State Science and Technology;* May, 1974, pages 689-692; in Cuthbert et al U.S. Pat. No. 3,790,287 issued Feb. 5, 1974; in Steigmeier et al U.S. Pat. No. 4,314,763 issued Feb. 9, 1982; and in commonly-owned Alford et al U.S. Pat. No. 4,376,583 issued Mar. 15, 1983.

In these known laser surface inspection systems, a laser beam is traversed across the surface of the silicon wafer and the reflections from the wafer surface are detected and analyzed to provide information about any defects present on the wafer surface. In the absence of defects, all of the light is specularly reflected from the surface. In locations where the beam strikes a surface defect, the light is scattered. The scattered and specularly reflected light may be separately collected and analyzed.

It is desirable in a laser inspection system to use as small a laser spot size as practical and to have it stay in focus as it moves over the area to be inspected. This usually means that the scanner must be some distance from the inspection surface and it must move through a relatively narrow angle.

The silicon wafers used in the manufacture of semiconductor devices have typically had a diameter ranging from about 5 to about 10 centimeters. However, semiconductor manufacturers have recognized that by using larger diameter silicon wafers, (20 centimeters have been shown recently) the semi-conductor devices can be produced in greater quantity and more economically. However, the wafer surface inspection systems presently available are limited in their ability to examine a wide inspection width.

In the wafer surface inspection system described in commonly-owned U.S. Pat. No. 4,376,583, for example, the scan beam B moves through a narrow angle $\theta$ and in an arc across the inspection surface, in a manner similar to that shown in FIG. 1, such that the scan beam is not always perpendicular to the surface. The reflected beam, R is divergent. For limited inspection widths, this is satisfactory, but the size and geometry of the laser scanning optics limits the scan width which can be covered by this approach.

An objective lens can be added, as shown in FIG. 2 at 16, to form a substantially parallel or collimated scan system. By this arrangement, the bundle of rays that form the spot can be reflected directly back through the objective lens 16 to a point detector 18 located near the scanner. The parallel or collimated scan system is more compact than a diverging scan because the light returned from the surface being inspected can pass back through the scan system to a point detector. This saves the need for fiber optics or other concentrating lenses ahead of the photodetector. In addition, a smaller sensitive area can be used in the detector to detect the entire scan. Also, the entire unit can be closer to the work so that more diffuse light can be gathered by intercepting a larger angle of the light that is scattered, resulting in better gain at the detector.

However, in order to inspect a relatively wide inspection width, the objective lens 16 must be correspondingly large, which is neither practical nor economically attractive.

In U.S. Pat. No. 4,314,763, a laser surface inspection system is disclosed wherein the scan beam is maintained perpendicular to the surface at all times. In this system, the beam is held still and the wafer is rotated under the beam to trace an Archimedes spiral as in playing a phonograph record. This system, however, would be undesirably slow, especially for wide inspection surfaces.

With the foregoing in mind, it is an object of the present invention to provide an improved laser scanning system suitable for use in a laser surface inspection system, and which is especially suited for covering a wide inspection width.

A further object of the invention is to provide a laser scanning system of the type described which is of compact and economical design and construction.

Still another object of the invention is to provide a compact laser scanning system which has a parallel scan pattern and maintains the flying laser spot in focus over the entire inspection width.

SUMMARY OF THE INVENTION

These and other objects and advantages are achieved in the present invention with the provision of a laser scanning system in which a folded optical cell is employed to provide an increased path of travel for the laser beam without correspondingly increasing the overall size of the scanning system.

The laser scanning system in accordance with the present invention comprises a laser source for producing a laser light beam; scanning means positioned for receiving and redirecting the laser beam so as to scan the beam in a predetermined plane; and a target positioned for receiving the scanned beam. The folded optical cell is interposed between the scanning means and the target and includes a pair of reflective surfaces which are so oriented with respect to one another as to cause the scanned beam to be reflected from each of the reflective surfaces a plurality of times in its course of travel from the scanning means to said target. This folded optical arrangement significantly increases the overall effective length of travel of the laser beam between the scanning means and the target, providing a corresponding increase in the depth of field.

The folded optical cell also serves to convert the divergent, curved scan pattern produced by the scanning means into a collimated, substantially parallel scan system. By this arrangement, the spectrally reflected light from the inspection surface reenters the optical cell and is concentrated at a photodetector.

The present invention also provides a unique and advantageous arrangement for collecting and concentrating substantially all of the diffuse light which is scattered by defects on the inspection surface. A collector is provided above the inspection surface having a reflective inner surface of an ellipsoidal configuration. The scan line produced by the scanning laser beam on the inspection surface is located at one focal point of the ellipsoid, and a light pipe is located at the other focal point. In this way, substantially all of the diffuse, scattered light which eminates from the scan line is reflected into and collected by the light pipe for detection by a photodetector.

BRIEF DESCRIPTION OF THE DRAWINGS

Some of the features and advantages of the invention having been stated, others will become apparent from the description which follows, when taken in connection with the accompanying drawings, in which—

FIG. 1 is a schematic view of a prior art laser scanning system in which the beam is scanned in arcuate path of travel across the inspection surface and produces a diverging reflected beam;

FIG. 2 is a schematic illustration showing how an objective lens can be added to the diverging scan system of FIG. 1 so that the scan beam moves substantially perpendicular to the surface;

FIG. 3 is an exploded perspective view of a laser surface inspection system in accordance with the present invention and showing the important elements in their approximate relationship to one another;

FIG. 6 is a schematic perspective view of a laser surface inspection system in accordance with a second form of the invention.

DESCRIPTION OF ILLUSTRATED EMBODIMENTS

While the present invention will be described more fully hereinafter with reference to the accompanying drawings, in which particular embodiments of the present invention are shown, it is to be understood at the outset that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

The present invention provides a laser scanning system which employs an optical cell on which the path of the laser beam is "folded", such that the same optical surface is used a plurality of times. More specifically, the cell includes a pair of opposed reflective surfaces which are so oriented as to cause the scanned beam to be reflected from each of the reflective surfaces a plurality of times. The folded optical cell thus functions like a series of thin lenses, and the actual physical result is a relatively long focal length and a correspondingly large depth of field within a relatively short space.

The drawings and detailed description which follow illustrate how this laser scanning system may be advantageously utilized in a laser surface inspection system for inspecting silicon wafers. Persons skilled in the applicable arts will recognize numerous other applications in which the laser scanning system may be used.

Figure 4:
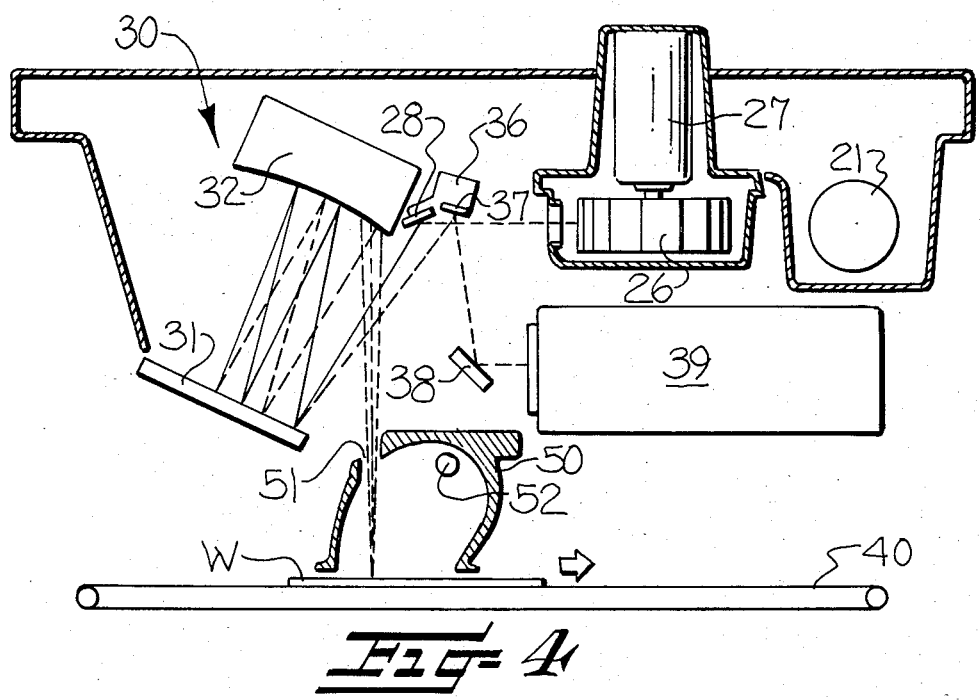
FIG. 4 is a side cross sectional view of the surface inspection system of FIG. 3.
Figure 5:
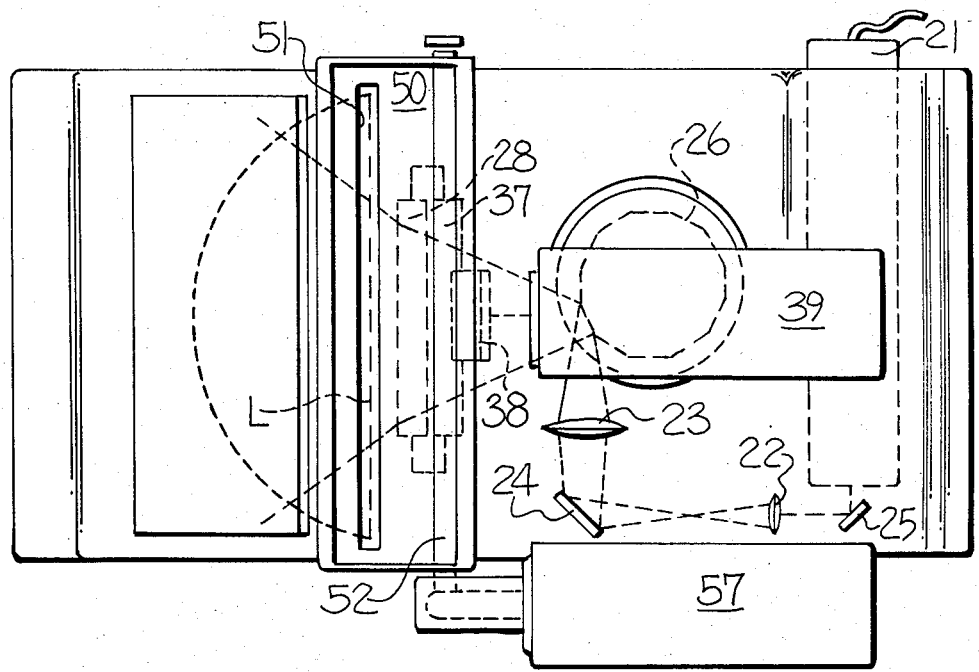
FIG. 5 is a plan view thereof.

The surface inspection system is shown in an exploded perspective form in FIG. 3, while a side cross sectional view of the same system is shown in FIG. 4 and a top plan view in FIG. 5. As illustrated, the incident laser beam B, shown in dashed lines in the drawings, eminates from a suitable laser source, such as a low wattage helium neon laser 21. The near collimated light from the laser 21, is focused by lenses 22 and 23 so as to form a small (e.g. 50 to 75 micron) diameter spot at a defined inspection surface corresponding to the upper surface of the silicon wafer W. After being turned by mirrors 24 and 25, the beam is directed onto a rotating scanning polygon mirror 26 of scanning means 27. The rotating mirror 26 causes the beam to move in a repeating scan pattern which traces a predetermined scan line, indicated at L, transversely across the wafer W or other inspection target.

As best seen in FIG. 4, from the scanner 27 the beam passes to an elongate bounce mirror 28, and then into the folded optical cell, generally indicated at 30. The optical cell 30 comprises a flat mirror 31 and a curved mirror 32, the reflective surfaces of which are mounted in opposed spaced apart relation to one another so that the laser beam, upon entering the cell from the primary bounce mirror 28, is reflected from each of the reflective surfaces a plurality of times prior to finally emerging from the cell, whereupon the beam is directed downwardly onto the surface of the inspection target. The number of bounces by the beam within the optical cell 30 can be determined by the entry and exit angles of the scan beam, as set by a pivotally mounted bounce bar 36. By folding the beam within the optical cell, such that it is reflected from each of the reflective surfaces a plurality of times, it is possible to significantly increase the overall effective length of travel of the laser beam between the scanning means and the inspection target, i.e. the focal length, within a very compact apparatus. By using a concave curved mirror 32 as one of the reflective surfaces of the optical cell 30 in combination with a planar mirror surface 31, the optical cell also converts the scanning path of the beam into a substantially collimated or parallel scan. Thus, the scanning beam remains substantially perpendicular to the inspection surface as it moves across the surface. Alternatively, the folded cell 30 may employ a pair of curved mirrors, and the optical cell can be set to produce either a parallel, a divergent, or a convergent scan pattern.

The particular curvature of the curved mirror 32 and the spacing with respect to the flat mirror 31 depend upon the specific details of the particular scanning system. In a wafer surface inspection apparatus of the embodiment illustrated in FIGS. 3 to 5, a curved cylindrical or parabolic mirror is preferred and the mirror spacing may typically range from 50 to 200 mm. By way of specific example, with a 1625 mm. parabola curved mirror 32 with 80 mm. spacing from the flat mirror 31, three or four bounces off the curved mirror 32 will give a 400 to 500 mm. effective pupil lens focal length. By adjusting the number of bounces or reflections off the curved mirror 32 and the spacing to the flat mirror 31, any effective focal length between about 250 and 750 mm. can be obtained from a 1625 mm. base parabola focal length.

Suitable means, such as a conveyor 40 is provided for advancing a silicon wafer W or other test article along a predetermined path of travel transversely of the scan line L of the laser beam with the surface of the wafer W located in a predetermined target plane.

The light which is reflected from the surface of the wafer may include both specularly reflected light and diffused light. These reflected light components are separately collected and converted by photodetectors to electrical signals for analysis to obtain information about the surface characteristics of the inspection target. For example, by sorting the signals with a comparator and keeping track of when they occur, a defect map of flaw type and location may be presented.

Since the incident laser beam is collimated and the scanning movement of the beam is substantially perpendicular to the surface of the wafer W, the specularly reflected beam passes back up through a slot 51 provided in the upper portion of collector 50 and reenters the optical cell 30, where it is reflected off of each of the reflective surfaces a plurality of times before finally leaving the optical cell and striking a bounce mirror 37, which is also carried by the pivotally mounted bounce bar 36. The beam is then redirected by a mirror 38 into a bright field photodetector 39. Since the beam is returning through the source optics, it converges to a point, and this point of convergence is coincident with the location of the bright field photodetector 39. In this way the scanning spectrally reflected beam is reconverted into a stationary point or spot for detection by the bright field photodetector 39.

The collector 50 which is located above the inspection surface has an inner reflective surface of an ellipsoidal configuration. The scattered light which is diffused from the inspection surface along the scan line L defines a line source of light. This line is placed at one focus of the ellipsoidal collector 50. At the second focus, a clear frosted light pipe 52 is mounted for collecting the diffused light and conveying it to a dark field photodetector 57. The collected diffused light thus emerges from the end of the light pipe 52, is redirected by suitably positioned mirrors 53, 54, and is convergingly focused onto the dark field photodetector 57 by a relay lens 55. It will thus be seen that the ellipsoidal shape of the collector 50 and the placement of the light pipe 52 and the scan line L at the foci of the ellipsoid results in substantially all of the scattered light from the surface of the wafer W being directed into and collected by the light pipe 51.

FIG. 6 illustrates a laser surface inspection system in accordance with an alternate form of the invention. This embodiment is similar in many respects to that previously described, and to avoid repetitive description of those elements which have already been described in detail, corresponding reference numerals will be used wherever applicable, with prime notation (') added.

Essentially, this embodiment differs over that previously described in that it is capable of collecting and analyzing three separate output channels of information, the bright and dark fields as in the previous embodiment, and in addition a third output channel of the "near" field light for enhanced detection of scratches or flaws that interrupt the specular surface. More specifically, the spectrally reflected beam is divided into a central bright field and a "near" field of spectrally reflected light surrounding the bright field.

As illustrated in FIG. 6, the bright field mirror 38' is so sized and positioned for reflecting only the central image portion of the spectrally reflected beam into the bright field detector 39'. The portions of the spectrally reflected beam surrounding the central bright field image are redirected by an overflow mirror 71 through a relay lens 72, and then from mirror 73 into a near field photodetector 70.

FIG. 6 also illustrates an alternate way of collecting the scattered light and directing this scattered light to the dark field detector 57'. As illustrated, a cylindrical light gathering lens 75 is mounted adjacent to a light pipe collector 73 for directing light into the collector 73 and thence to the dark field photodetector 57'.

To further enhance the signal to noise ratio of the system, opaque shields or "stops", indicated at 80, may be mounted between the planes of the incident scan beam and the spectrally reflected scan beam. This is possible since the respective incident and reflected beams move in planes which are angularly offset to one another. The shields or stops 80 may be mounted between the optical cell 30' and the target, and/or between the optical cell 30' and the bounce mirrors 28', 36'.

The information collected by the respective photodetectors may be processed via suitable interface electronics and computer means, to provide important information about the nature, severity and location of the defects present on the surface of the wafer. A detailed description of one suitable method which has been employed for flaw measurement and classification is contained in commonly-owned U.S. Pat. No. 4,376,583.

That which is claimed is:

1. A laser scanning system comprising
   (a) a laser source for producing a laser light beam;
   (b) a polygonal mirror positioned for receiving and reflecting the laser beam, said polygonal mirror being mounted for rotation so as to cause the laser beam to scan along an arcuate path of travel in a predetermined plane;
   (c) a target positioned for receiving the scanned beam; and
   (d) a folded optical cell interposed between the scanning means and the target, said cell including a pair of mirrors mounted in opposed spaced apart relation and including respective reflective surfaces so oriented with respect to one another as to cause the scanned beam to be reflected from each of the reflective surfaces a plurality of times in its course of travel from said polygonal mirror to said target to thereby significantly increase the overall effective length of travel of the laser beam between the polygonal mirror and the target.

2. A laser scanning system according to claim 1 wherein one of said pair of mirrors has a planar reflective surface and the opposing mirror has a concave parabolic reflective surface effective to cause the scanning beam to move in a collimated, parallel scan pattern.

3. A laser scanning system according to claim 1 wherein said target lies in a predetermined target plane and has predetermined length and width dimensions, wherein said scanning system additionally includes means for moving the target while in said target plane along a predetermined path of travel extending transversely of the arcuate scan path of the laser beam so that the entire length and width of the target is scanned by the laser beam during said movement of the target.

4. A laser surface inspection system comprising
(a) a laser source for producing a laser light beam;
(b) scanning means positioned for receiving and redirecting the laser beam so as to scan in a predetermined plane;
(c) a target positioned for receiving the scanned beam;
(d) a folded optical cell interposed between the scanning means and the target and including a pair of reflective surfaces so oriented with respect to one another as to cause the scanned beam to be reflected from each of the reflective surfaces a plurality of times in its course of travel from said scanning means to said target to thereby significantly increase the overall effective length of travel of the laser beam between the scanning means and the target; and
(e) detector means positioned for receiving light reflected from said target and for determining therefrom the surface characteristics of the target.

5. A laser surface inspection system according to claim 4 wherein said detector means includes a dark field light detector and means for directing scattered light which is reflected from the surface of said target into said dark field light detector.

6. A laser surface inspection system according to claim 4 wherein said detector means includes a bright field light detector and means for directing light which is specularly reflected from the target into said bright field light detector, said bright field light detector being so positioned that the specularly reflected beam is directed into said folded optical cell and is reflected from each of the reflective surfaces thereof a plurality of times in its course of travel from the target to said bright field light detector.

7. A laser surface inspection system according to claim 6 wherein said means for directing specularly reflected light into said bright field light detector includes means for directing only the central image portion of the specularly reflected beam into said bright field light detector and wherein said detector means additionally includes a near field light detector and means for directing the remaining surrounding portion of the specularly reflected beam surrounding said central image portion into said near field light detector.

8. A laser surface inspection system comprising
(a) a laser source for producing a laser light beam;
(b) scanning means positioned for receiving and redirecting the laser beam so as to scan in a predetermined plane;
(c) a target having an inspection surface positioned for receiving the scanned beam;
(d) a folded optical cell interposed between the scanning means and the target and including a pair of reflective surfaces so oriented with respect to one another as to cause the scanned beam to be reflected from each of the reflective surfaces a plurality of times in its course of travel from said scanning means to said target to thereby significantly increase the overall effective length of travel of the laser beam between the scanning means and the target; and
(e) detector means positioned for receiving light reflected from said target and for determining therefrom the surface characteristics of the target, said detector means including a light detector, a light tube optically connected to said light detector, and an ellipsoidal mirror located adjacent to the inspection surface and being so positioned that the intersection of the laser scan line with the inspection surface and the longitudinal axis of said light tube lie at the respective foci of the ellipsoidal mirror whereby substantially all of the scattered light which is reflected from the inspection surface along said scan line is directed into the light tube.

9. A laser surface inspection system comprising
(a) a laser source for producing a laser light beam;
(b) scanning means positioned for receiving and redirecting the laser beam so as to scan in a predetermined plane and along a predetermined scan line;
(c) means for advancing a test article along a predetermined path of travel transversely of said scan line and with the inspection surface of the test article positioned in a predetermined target plane for receiving the scanned beam thereacross;
(d) a folded optical cell interposed between the scanning means and the test article and including a pair of mirrors mounted in opposed spaced apart relation and including respective reflective surfaces so oriented with respect to one another as to cause the scanned beam to be reflected from each of the reflective surfaces a plurality of times in its course of travel from said scanning means to the inspection surface to thereby significantly increase the overall effective length of travel of the laser beam between the scanning means and the inspection surface; and
(e) detector means positioned for receiving light reflected from the inspection surface, said detector means including a dark field light detector and means for directing scattered light which is reflected from said surface into said dark field light detector, and said detector means also including a bright field light detector and means for directing light specularly reflected from said surface into said bright field light detector.

10. A laser surface inspection system according to claim 9 wherein said bright field light detector is so positioned that the specularly reflected beam from the inspection surface is directed into said folded optical cell and is reflected from the respective reflective surfaces thereof a plurality of times in its course of travel from the surface to said bright field light detector.

11. A laser surface inspection system according to claim 10 wherein the path of travel of said specularly reflected beam between the inspection surface and said optical cell is in a plane different from said predetermined plane of the incident scanning beam, and including an opaque shield located between the planes of the incident beam and the reflected beam for isolating the reflected beam from the incident beam.

12. A laser surface inspection system according to claim 9 wherein said means for directing scattered light into said dark field light detector comprises a light tube optically connected to said dark field light detector for receiving light and conducting it into said detector, and an ellipsoidal mirror located adjacent to the inspection surface and being so positioned that the intersection of the laser scan line with the inspection surface and the longitudinal axis of said light tube lie at the respective foci of the ellipsoidal mirror whereby substantially all of the scattered light which is reflected from the inspection surface along said scan line is directed into the light tube.

13. A laser surface inspection system according to claim 9 including a pair of photodetector means located at each end of the path of the scanning laser beam for sensing the beginning and end of each scan of the laser beam.

* * * * *